United States Patent
Chen et al.

(10) Patent No.: US 11,617,610 B2
(45) Date of Patent: Apr. 4, 2023

(54) SYSTEM AND METHOD FOR MICRO-SIZED COLD ATMOSPHERIC PLASMA TREATMENT

(71) Applicant: US Patent Innovations, LLC, Takoma Park, MD (US)

(72) Inventors: Zhitong Chen, Ashburn, VA (US); Jerome Canady, Lakeland, FL (US); Michael Keidar, Baltimore, MD (US)

(73) Assignee: US Patent Innovations LLC, Takoma Park, MD (US)

( * ) Notice: Subject to any disclaimer, the term of this patent is extended or adjusted under 35 U.S.C. 154(b) by 372 days.

(21) Appl. No.: 16/392,054

(22) Filed: Apr. 23, 2019

(65) Prior Publication Data
US 2019/0328440 A1 Oct. 31, 2019

Related U.S. Application Data

(60) Provisional application No. 62/662,795, filed on Apr. 26, 2018.

(51) Int. Cl.
*A61B 18/04* (2006.01)
*A61B 18/00* (2006.01)

(52) U.S. Cl.
CPC .. *A61B 18/042* (2013.01); *A61B 2018/00583* (2013.01); *H05H 2245/30* (2021.05)

(58) Field of Classification Search
CPC ........ A61B 18/042; A61B 2018/00583; A61B 2018/00196; H05H 2245/122
See application file for complete search history.

(56) References Cited

U.S. PATENT DOCUMENTS 3,467,471 A * 9/1969 Thomas ................. G01N 21/73
356/36
5,938,950 A 8/1999 Gay et al.
(Continued)

FOREIGN PATENT DOCUMENTS

| WO | WO-2012158443 A2 * | 11/2012 | ................ A61N 1/44 |
| WO | WO-2012167089 A1 * | 12/2012 | ........... A61B 18/042 |
| WO | 2018191265 A1 | 10/2018 | |

OTHER PUBLICATIONS

Keidar, M. Plasma for cancer treatment. Plasma Sources Science and Technology 24, 033001 (2015).
(Continued)

*Primary Examiner* — Linda C Dvorak
*Assistant Examiner* — Lindsay Regan Lancaster
(74) *Attorney, Agent, or Firm* — 24IP Law Group USA, PLLC; Timothy R DeWitt

(57) ABSTRACT

A micro-sized cold atmospheric plasma accessory. The micro-sized cold atmospheric plasma accessory comprises a tube, an active electrode within said tube, and a nozzle at a distal end of said tube, said nozzle having an inner diameter less than 1 mm and a length less than 30 mm. A distal end inner diameter of said tube is greater than said inner diameter of said nozzle. The nozzle preferable is 15-25 mm in length. The nozzle may comprise stainless steel. The tube may have an inner diameter greater than 1 mm. The nozzle preferably has a distal end inner diameter less than 280 μm. The micro-sized cold atmospheric plasma accessory may further comprise a return electrode on an outside of said tube. The tube may comprise a quartz tube

10 Claims, 8 Drawing Sheets

(56) References Cited

U.S. PATENT DOCUMENTS

| | | | |
|---|---|---|---|
| 7,608,839 B2* | 10/2009 | Coulombe | H01T 23/00 250/426 |
| 9,999,462 B2 | 6/2018 | Canady et al. | |
| 10,213,614 B2 | 2/2019 | Keidar et al. | |
| 2011/0101862 A1 | 5/2011 | Koo et al. | |
| 2013/0327856 A1* | 12/2013 | Fukanuma | B05B 15/18 239/601 |
| 2014/0370203 A1* | 12/2014 | Sailer | H05K 3/14 427/455 |
| 2015/0246471 A1* | 9/2015 | Corazza | B29C 45/278 425/568 |
| 2017/0354453 A1 | 12/2017 | Krasik et al. | |

OTHER PUBLICATIONS

Keidar, M. et al. Cold plasma selectivity and the possibility of a paradigm shift in cancer therapy. British journal of cancer 105, 1295-1301 (2011).

Dezest, M. et al. Mechanistic insights into the impact of Cold Atmospheric Pressure Plasma on human epithelial cell lines. Scientific reports 7 (2017).

Cheng, X. et al. The effect of tuning cold plasma composition on glioblastoma cell viability. PloS one 9, e98652 (2014).

Attri, P. et al. Influence of ionic liquid and ionic salt on protein against the reactive species generated using dielectric barrier discharge plasma. Scientific reports 5, 17781 (2015).

Yan, D.; Sherman, J. H.; Cheng, X.; Ratovitski, E.; Canady, J.; Keidar, M. Controlling plasma stimulated media in cancer treatment application. Appl. Phys. Lett. 2014, 105, 224101.

Yan D, Sherman JH, and Keidar M. Cold atmospheric plasma, a novel promising anticancer modality. Oncotarget. 11, 2016, 113304.

Dikalov, S. I. & Harrison, D. G. Methods for detection of mitochondrial and cellular reactive oxygen species. Antioxidants & redox signaling 20, 372-382 (2014).

Kalghatgi, S., Friedman, G., Fridman, A. & Clyne, A. M. Endothelial cell proliferation is enhanced by low dose non-thermal plasma through fibroblast growth factor-2 release. Annals of biomedical engineering 38, 748-757 (2010).

Chen, Z., Lin, L., Cheng, X., Gjika, E. & Keidar, M. Treatment of gastric cancer cells with nonthermal atmospheric plasma generated in water. Biointerphases 11, 031010 (2016).

Scholtz, V., Julák, J. & Krlha, V. The Microbicidal Effect of Low-Temperature Plasma Generated by Corona Discharge: Comparison of Various Microorganisms on an Agar Surface or in Aqueous Suspension. Plasma Processes and Polymers 7, 237-243 (2010).

Mirpour, S. et al. Utilizing the micron sized nonthermal atmospheric pressure plasma inside the animal body for the tumor treatment application. Scientific reports 6, 29048 (2016).

Jaraslov Jansky et al. "Stinulation of the discharge propagation in capillary tube in teh air at atmospheric pressure," 2010 J.Phys. D: Appl. Phys. 43 3952-1.

Binnebaum, et al., "Cold Atmospheric Plasma, Created at the Tip of an Elongated Flexible Capillary Using Low Electric Current, Can Slow the Progression of Melanoma," Plos One (2017).

* cited by examiner

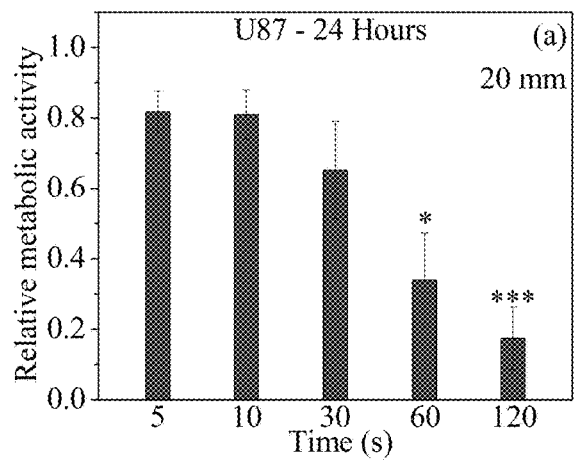
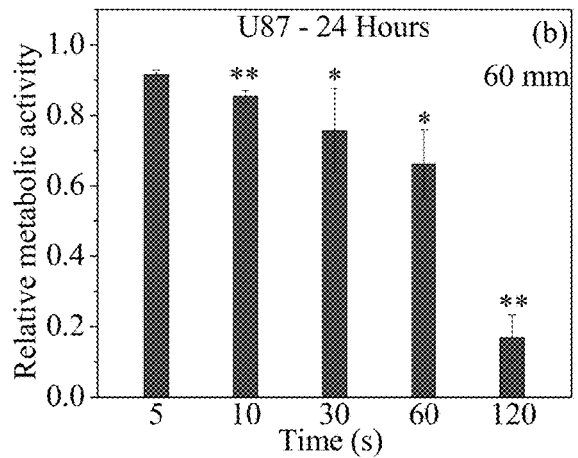
FIG. 6A            FIG. 6B
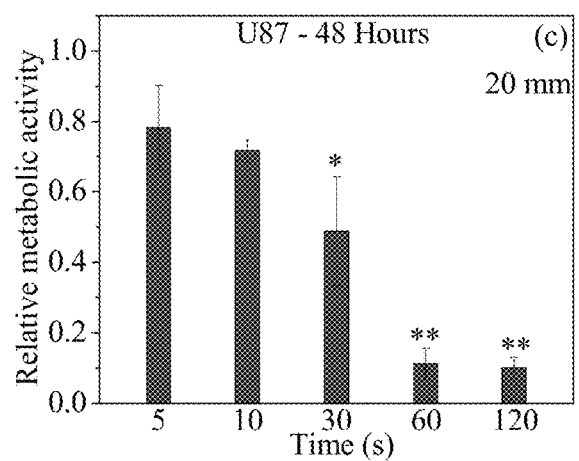
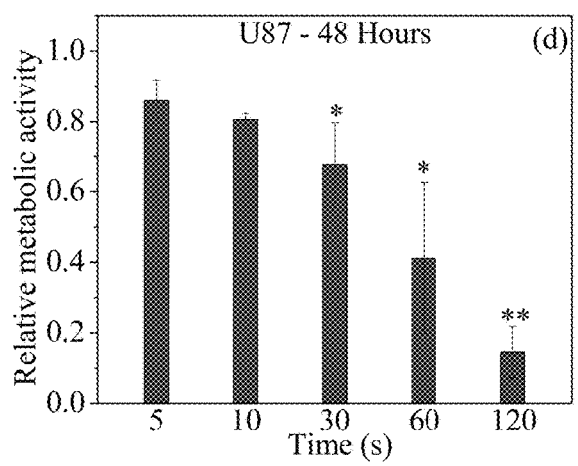
FIG. 6C            FIG. 6D

SYSTEM AND METHOD FOR MICRO-SIZED COLD ATMOSPHERIC PLASMA TREATMENT

CROSS-REFERENCE TO RELATED APPLICATIONS

The present application claims the benefit of the filing date of U.S. Provisional Patent Application Ser. No. 62/662,795 filed by the present inventors on Apr. 26, 2018. The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to devices and methods for application of cold atmospheric plasma to brain and breast cancer.

Brief Description of the Related Art

Cold atmospheric plasma (CAP) has been proposed as a novel therapeutic method for anticancer treatment, which can be applied to living tissues and cells. See, Keidar, M. Plasma for cancer treatment. *Plasma Sources Science and Technology* 24, 033001 (2015); Keidar, M. et al. Cold plasma selectivity and the possibility of a paradigm shift in cancer therapy. *British journal of cancer* 105, 1295-1301 (2011). Several systems for performing cold atmospheric plasma procedures and have been developed, including the systems disclosed in U.S. Pat. Nos. 10,213,614, 9,999,462, and International Application Publication WO 2018/191265.

CAP is a partially ionized gas that contain charge particles, reactive oxygen and nitrogen species (ROS and RNS), excited atoms, free radicals, UV photons, electric field, etc. See, Dezest, M. et al. Mechanistic insights into the impact of Cold Atmospheric Pressure Plasma on human epithelial cell lines. *Scientific reports* 7 (2017); Cheng, X. et al. The effect of tuning cold plasma composition on glioblastoma cell viability. *PloS one* 9, e98652 (2014). ROS and RNS, combined or independently, are well known to initiate different signaling pathways in cells and to promote oxidative stress. See, Attri, P. et al. Influence of ionic liquid and ionic salt on protein against the reactive species generated using dielectric barrier discharge plasma. *Scientific reports* 5, 17781 (2015); Yan, D.; Sherman, J. H.; Cheng, X.; Ratovitski, E.; Canady, J.; Keidar, M. Controlling plasma stimulated media in cancer treatment application. Appl. Phys. Lett. 2014, 105, 224101. Plasma-induced biological effects include damage lips, proteins, DNA, and induce apoptosis through plasma-generated ROS and RNS. See, Yan D, Sherman J H, and Keidar M. Cold atmospheric plasma, a novel promising anticancer modality. Oncotarget. 11, 2016, 113304; Dikalov, S. I. & Harrison, D. G. Methods for detection of mitochondrial and cellular reactive oxygen species. Antioxidants & redox signaling 20, 372-382 (2014); Kalghatgi, S., Friedman, G., Fridman, A. & Clyne, A. M. Endothelial cell proliferation is enhanced by low dose non-thermal plasma through fibroblast growth factor-2 release. *Annals of biomedical engineering* 38, 748-757 (2010). Moreover, many studies have reported both in vivo and vitro that plasma is a possible adjunct treatment in oncology as well as killing achieved for various types of cancers such as glioblastoma, breast cancer, bladder carcinoma, cervical carcinoma, skin carcinoma, pancreatic carcinoma, lung carcinoma, colon carcinoma, gastric carcinoma, melanoma and hepatocellular carcinoma. See, for example, Chen, Z., Lin, L., Cheng, X., Gjika, E. & Keidar, M. Treatment of gastric cancer cells with nonthermal atmospheric plasma generated in water. *Biointerphases* 11, 031010 (2016).

In plasma medicine, jet plasma, corona discharge, and dielectric barrier discharge (DBD) have been used. Scholtz, V., Julák, J. & Křiha, V. The Microbicidal Effect of Low-Temperature Plasma Generated by Corona Discharge: Comparison of Various Microorganisms on an Agar Surface or in Aqueous Suspension. *Plasma Processes and Polymers* 7, 237-243 (2010). These types of plasma can be directly applied to skin cancers, while they are not applicable for more systemic cancer treatment. Some studies investigated the plasma device in the micro-sized to conduct the plasma species to the living animals. Mirpour, S. et al. Utilizing the micron sized non-thermal atmospheric pressure plasma inside the animal body for the tumor treatment application. *Scientific reports* 6, 29048 (2016). However, their device just applied to xenografts tumors not systemic cancer treatment and used a 250 µm capillary tube 5 cm in length.

SUMMARY OF THE INVENTION

Micro-sized cold atmospheric plasma (µCAP) has been developed to expand the applications of CAP in cancer therapy. Delivery of the plasma species is crucial to suppress tumor growth and assess efficiency of micro-sized plasma device. Hence, the present work designed micro-sized cold atmospheric plasma devices with different lengths of nozzle in order to enhance delivery of reactive species and evaluate the efficiency of these devices on cancer therapy.

In this application, µCAP devices with different nozzle lengths were applied to investigate effects on both brain (glioblastoma U87) and breast (MDA-MB-231) cancer cells. Various diagnostic techniques were employed to evaluate the parameters of µCAP devices with different lengths such as potential distribution, electron density, and optical emission spectroscopy. The generation of short- and long-lived species (such as hydroxyl radical (•OH), superoxide ($O_2^-$), hydrogen peroxide ($H_2O_2$), nitrite ($NO_2^-$), et al) were studied. These data revealed that µCAP treatment with a 20 mm length tube has a stronger effect than that of the 60 mm tube due to the synergetic effects of reactive species and free radicals. Reactive species generated by µCAP enhanced tumor cell death in a dose-dependent fashion and was not specific with regards to tumor cell type.

In a preferred embodiment, the present invention is a micro-sized cold atmospheric plasma accessory. The micro-sized cold atmospheric plasma accessory comprises a tube, an active electrode within said tube, and a nozzle at a distal end of said tube, said nozzle having an inner diameter less than 1 mm and a length less than 30 mm. A distal end inner diameter of said tube is greater than said inner diameter of said nozzle. The nozzle preferable is 15-25 mm in length. The nozzle may comprise stainless steel. The tube may have an inner diameter greater than 1 mm. The nozzle preferably has a distal end inner diameter less than 280 µm. The micro-sized cold atmospheric plasma accessory may further comprise a return electrode on an outside of said tube. The tube may comprise a quartz tube.

In another preferred embodiment, the present invention is a method for treating cancerous tissue with cold atmospheric plasma. The method comprises causing an inert gas to flow through a tube toward target tissue, applying electrosurgical energy to an electrode within said tube to plasmatize gas flowing through said tube; causing said plasma to flow out of a nozzle at a distal end of said tube, said nozzle having an inner diameter less than 1 mm and a length less than 30 mm, and applying said plasma flowing out of said nozzle to target tissue.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 6A-6D show cell viability of U87 after 24 and 48 hours' incubation with μCAP treatment with 20 mm and 60 mm length during 5, 10, 30, 60, and 120 seconds' treatment. Cell viability of U87 treated by 20 mm He μCAP at (a) 24-h incubation and (c) 48-h incubation. Cell viability of U87 treated by 60 mm He μCAP at (b) 24-h incubation and (d) 48-h incubation. The ratios of surviving cells for each cell line were normalized relative to controls (DMEM). Student t-test was performed, and the statistical significance compared to cells present in DMEM is indicated as *$p<0.05$, $p<0.01$, *$p<0.005$. (n=3)

DETAILED DESCRIPTION OF THE PREFERRED EMBODIMENTS

Figure 1A:
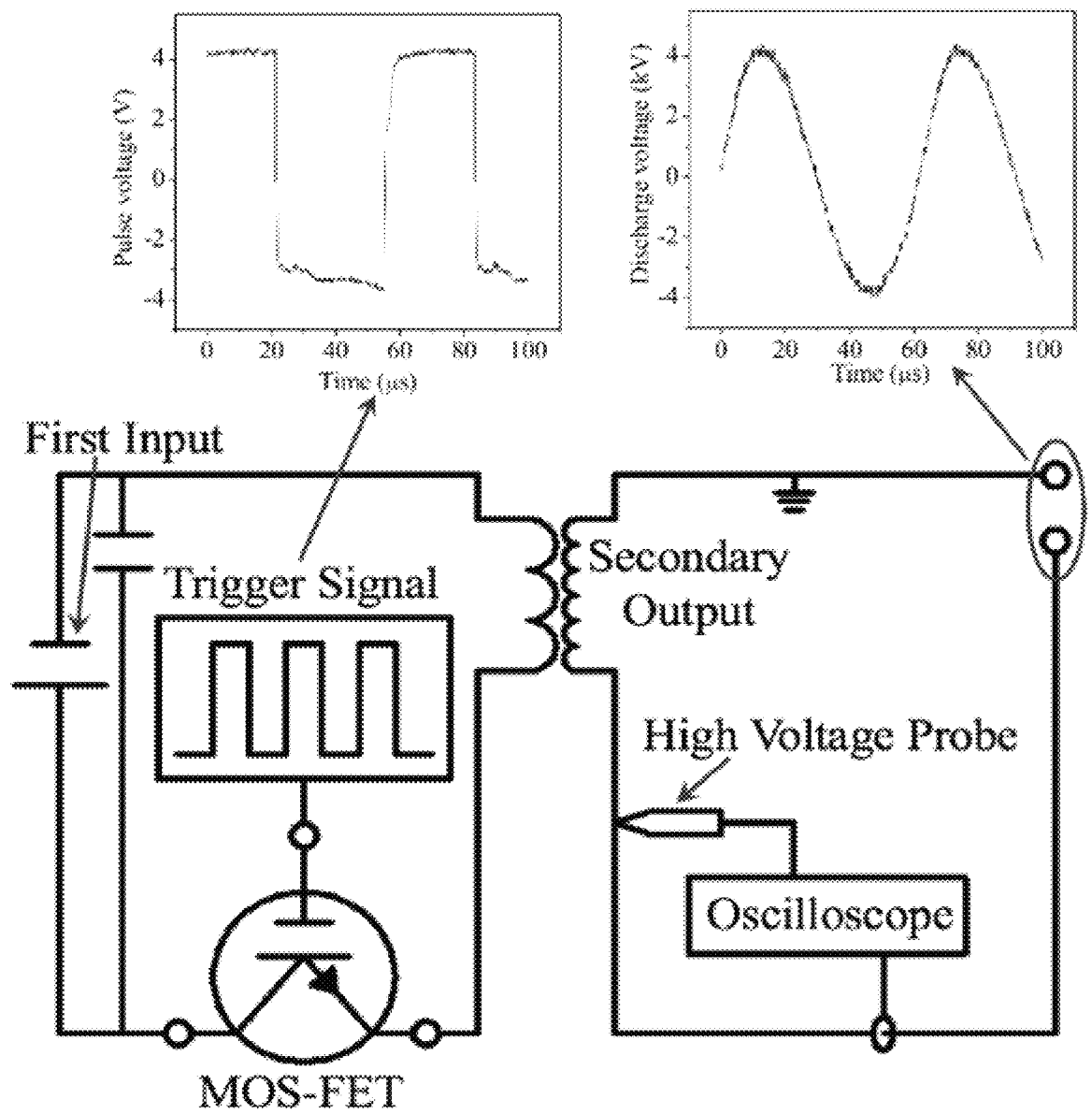
FIGS. 1A, 1B and 1C are schematic representations of the experiment setup including high voltage power part (FIG. 1A) and the micro-sized cold atmospheric plasma with 20 mm and 60 mm length of stainless steel tubes (FIGS. 1B and 1C).
Figure 1B:
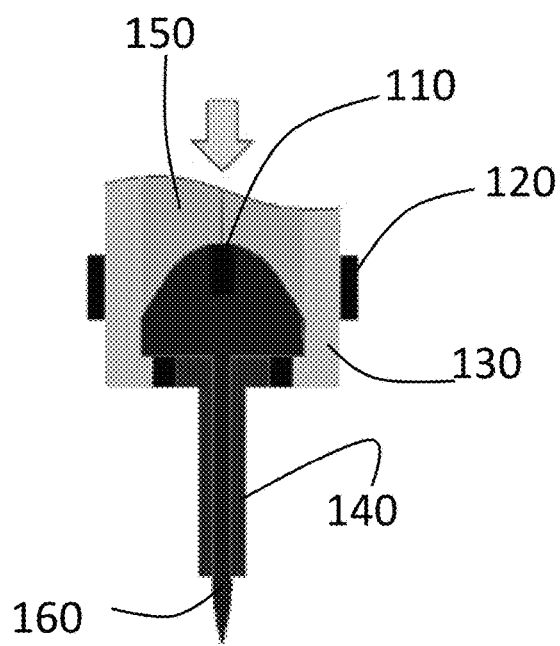
Figure 1C:
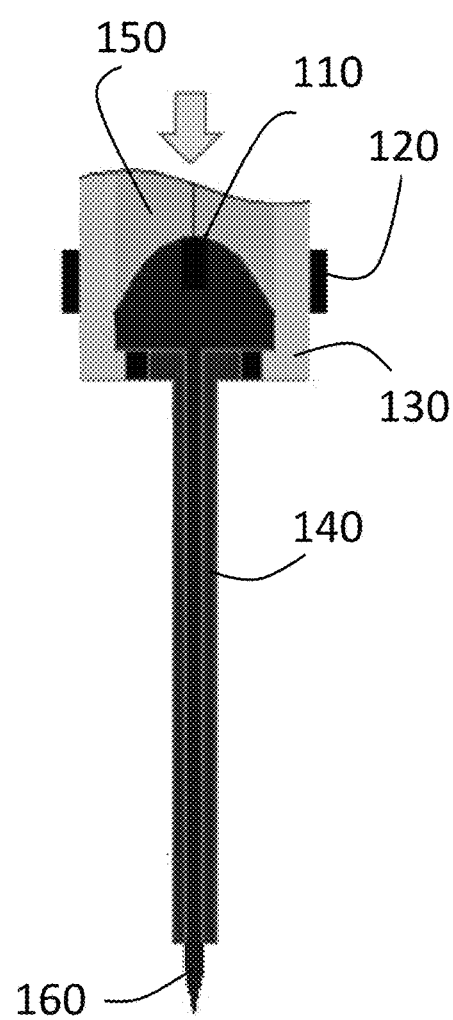

FIGS. 1A, 1B and 1C depict the schematic of the experiment setup including high voltage power (FIG. 1A) and μCAP devices (FIGS. 1B and 1C). The high voltage power includes DC input, Trigger signal+MOSFET (switch), and the secondary output. In this work, the DC input was set at 5 V, square wave signal was obtained from the control unit (upper left in FIG. 1A), and a high voltage wave was obtained from the square wave signal through the transformer (upper right in FIG. 1A). Each μCAP device consist of a two-electrode (copper) assembly with a central powered electrode 110 (1 mm in diameter) and a grounded outer electrode 120 wrapped around the outside of a quartz tube 130 (10 mm) as shown in FIGS. 1B and 1C. The central electrodes 110 were connected to the secondary output of the high voltage transformer. The peak-peak voltage was approximately 8 kV and the frequency of the discharge was around 16 kHz (upper right in FIG. 1A). At the end of the quartz tube 130, a 275±5 μm inner diameter capillary tube 140 (stainless steel) was attached and insulated by epoxy. As shown in FIG. 1B, the capillary tube was 20 mm in length, while in FIG. 1C the capillary tube was 60 mm in length. The feed gas 140 for this study was industrial purity helium, which was injected into the quartz tube 110 with a 0.2 L/min gas flow rate. A longer tube (e.g., 60 mm) is needed to access deeper tumors in brain and breast. When electrically energy is applied to the central electrode (and the outer electrode is grounded), the gas 150 forms a plasma 160 that flows out of the end of the capillary tube 140.

While the experimental setup used a cold plasma system of a type similar to that disclosed in U.S. Pat. No. 10,213,614 in the sense that is uses two electrodes, it will be apparent to one of skill in the art that if a converter box such as is disclosed in U.S. Pat. No. 9,999,462, or a hybrid generator such as is disclosed in International Application Publication WO 2018/191265 the outer electrode 120 can be eliminated from the setup.

In the experiments, the effect of tube length was studied to understand limitations of depth. For instance, it is believed that a longer tube (60 mm) is needed to access deeper tumors in brain and breast. UV-visible-NIR, a range of wavelength 200-850 nm, was investigated on plasma to detect various RNS and ROS (nitrogen [$N_2$], nitric oxide [—NO], nitrogen cation [$N^{+2}$], atomic oxygen [O], and hydroxyl radicals [—OH]). The optical probe was placed at distance of 1.0 cm in front of the plasma jet nozzle. Data were then collected with an integration time of 100 ms.

A fluorimetric hydrogen peroxide assay Kit (Sigma-Aldrich) was used for measuring the amount of $H_2O_2$, according to the manufacturer's protocol. Briefly, 50 μl of standard curve, control, and experimental samples were added to 96-well flat-bottom black plates, and then 50 μl of Master Mix was added to each of well. The plates were incubated for 20 min at room temperature protected from light and fluorescence was measured by a Synergy H1 Hybrid Multi-Mode Microplate Reader at Ex/Em: 540/590 nm.

RNS level were determined by using a Griess Reagent System (Promega Corporation) according to the instructions provided by the manufacturer. Briefly, 50 of samples and 50 of the provided Sulfanilamide Solution were added to 96-well flat-bottom plates and incubated for 5-10 minutes at room temperature. Subsequently, 50 µl of the NED solution was added to each well and incubated at room temperature for 5-10 minutes. The absorbance was measured at 540 nm by Synergy H1 Hybrid Multi-Mode Microplate Reader.

XTT sodium salt ((2,3-bis(2-methoxy-4-nitro-5-sulfophenyl)-5-[(phenylamino)carbonyl]-inner salt-2H-tetrazolium, monosodium salt)) solution, purchased from Cayman chemical, was prepared by dissolving XTT power in DMEM. XTT sodium salt solution (100 µl per well, 500 µM) in a 96-well flat-bottom plate by µCAP for 5, 10, 30, 60, and 120 seconds. The gap between the outlet of µCAP and the surface of the samples was set at approximately 3 mm. As a control, untreated XTT sodium salt solution in triplicate were transferred to a 96-well flat-bottom plate. As a control, DMEM (100 µl per well) was treated with µCAP for 5, 10, 30, 60, and 120 seconds. The color change of XTT solution was used to indicate the presence of superoxide ($O_2^-$). A color change of XTT solution was measured by Hach DR 6000 uv vis spectrophotometer at 470 nm.

A MB solution was prepared by dissolving MB power in DMEM. MB solutions (100 µl per well, 0.01 g/L) in a 96-well flat-bottom plate were treated by µCAP for 5, 10, 30, 60, and 120 seconds. The gap between the outlet of µCAP and the surface of the samples was approximately 3 mm. As a control, untreated MB solutions in triplicate were transferred to a 96-well flat-bottom plate. The color change of methylene blue shows the presence of OH radicals via immediate and distinct bleaching of methylene blue dye (qualitatively analysis). The color change of the MB solution was measured as the absorbance at 664 nm by a Synergy H1 Hybrid Multi-Mode Microplate Reader.

Human glioblastoma cancer cells (U87MG, Perkin Elmer) were cultured in Dulbecco's Modified Eagle Medium (DMEM, Life Technologies) supplemented with 10% (v/v) fetal bovine serum (Atlantic Biologicals) and 1% (v/v) penicillin and streptomycin (Life Technologies). Cultures were maintained at 37° C. in a humidified incubator containing 5% (v/v) $CO_2$. The human breast cancer cell line (MDA-MB-231) was cultured in Dulbecco's Modified Eagle Medium (DMEM, Life Technologies) supplemented with 10% (v/v) foetal bovine serum (Atlantic Biologicals) and 1% (v/v) penicillin and streptomycin (Life Technologies). Cultures were maintained at 37° C. in a humidified incubator containing 5% (v/v) $CO_2$.

U87 and MDA-MB-231 cells were plated in 96-well flat-bottom microplates at a density of 3000 cells per well in 100 µL of complete culture medium. Cells were incubated for 24 hours to ensure proper cell adherence and stability. On day 2, the cells were treated by He µCAP for 0, 5, 10, 30, 60, and 120 seconds. Cells were further incubated at 37° C. for 24 and 48 hours. The cell viability of the glioblastoma and breast cancer cells were measured for each incubation time point with an MTT assay. 100 µL of MTT solution (3-(4,5-dimethylthiazol-2-yl)-2,5-diphenyltetrazolium bromide) (Sigma-Aldrich) was added to each well followed by a 3-hour incubation. The MTT solution was discarded and 100 µL per well of MTT solvent (0.4% (v/v) HCl in anhydrous isopropanol) was added to the wells. The absorbance of the purple solution was recorded at 570 nm with a Synergy H1 Hybrid Multi-Mode Microplate Reader.

Figure 2A:
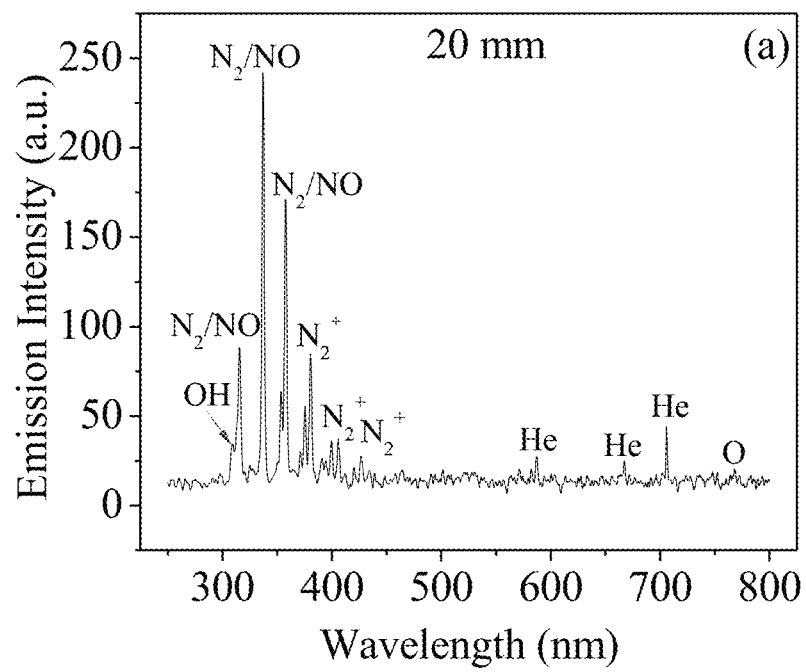
FIGS. 2A and 2B show optical emission spectrum detected from the He μCAP with 20 mm (FIG. 2A) and 60 mm (FIG. 2B) length's tube using UV-visible-NIR, in the 250-850 nm wavelength range.
Figure 3A:
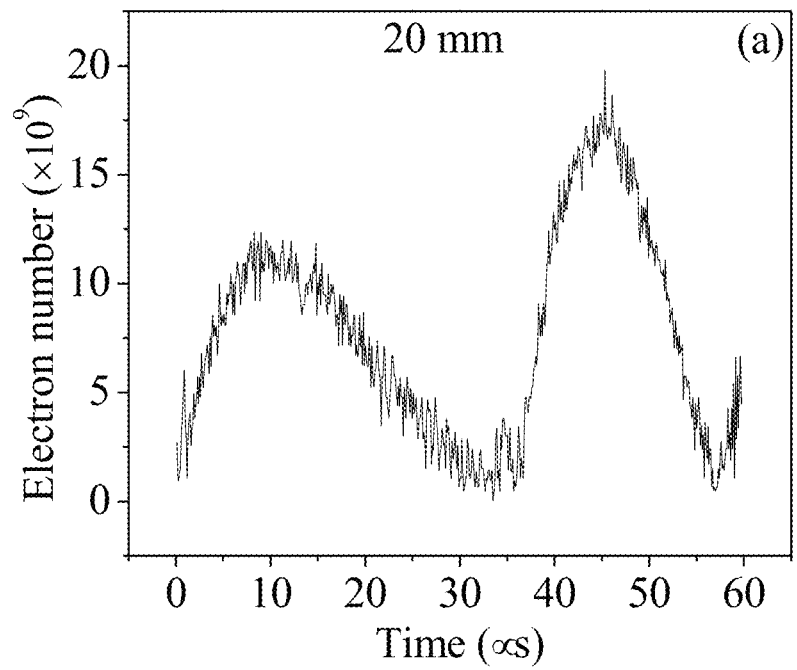
FIGS. 3A and 3B show the electron number of 20 mm (a) and 60 mm (b) length μCAP
Figure 3B:
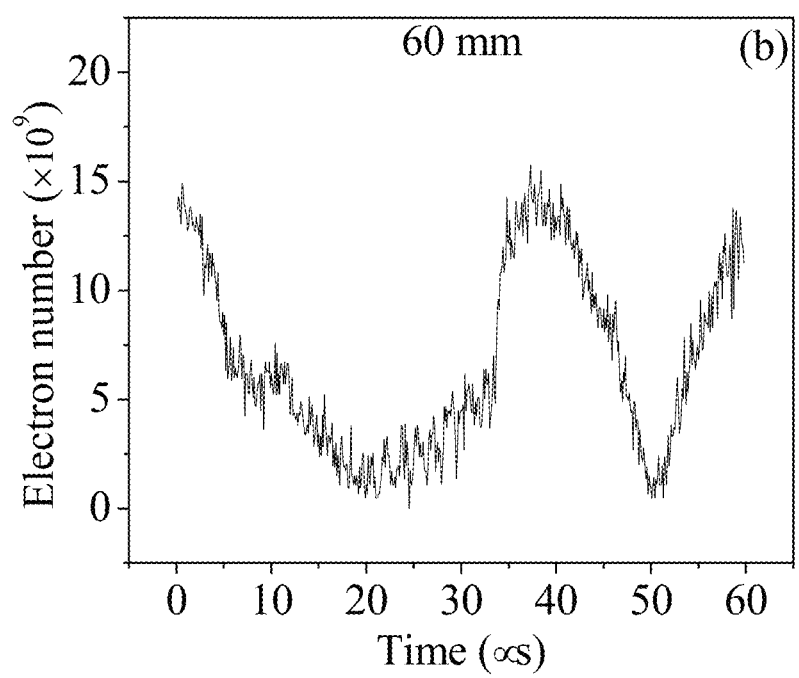

The reactive species generated by the µCAP device with different micro-sized tube length are detected by optical emission spectroscopy, as shown in FIG. 2A. The identification of the emission line and bands was performed mainly according to reference[29]. For 20 mm and 60 mm length devices, an $N_2$ second-positive system (315 nm, 337 nm 357 nm, and 380 nm) representing the photon emission intensity drops from the state $C^3\Pi u$ to $\beta^3\Pi g$ with different upper and lower vibration quantum numbers. There are very weak emission lines in the special range of 250-300 nm, which are detected as NO lines. The helium bands were assigned between 500 and 750 nm as shown in FIGS. 3a and 3b. We also observed a high-intensity $OH/O_3$ peak at 309 nm for both 20 mm and 60 mm length devices. Atomic oxygen (O, including the ground state and all the excited states of atomic oxygen) was observed at 777 nm in both devices, which was believed to have a significant effect on cells and therefore a broad biomedical application. Micro-sized plasma is a complicated environment that combines the comprehensive effect of different ions and reactive species. The 60 mm µCAP has a bit less electron and species than 20 mm µCAP due to long distance delivery.

The experimental Rayleigh microwave scattering (RMS) system was described previously. See, Chen, Z., Cheng, X., Lin, L. & Keidar, M. Cold atmospheric plasma discharged in water and its potential use in cancer therapy. *Journal of Physics D: Applied Physics* 50, 015208 (2016). The detection of the scattered signal was accomplished using a homodyne scheme by means of an I/Q mixer, providing in-phase (I) and quadrature (Q) outputs. For the entire range of scattered signals, the amplifiers and mixer were operated in linear mode. The total amplitude of the scattered microwave signal was determined by: $U=\sqrt{I^2+Q^2}$. We can calculate the total electron number in the plasma as $N_e=U(w^2+v_m^2)/(2.82\times10^{-4}Av_m)$, where w is the angular frequency, $v_m$ is the frequency of the electron-neutral collisions, and A is the proportionality coefficient. See, Lin, L. & Keidar, M. Cold atmospheric plasma jet in an axial DC electric field. *Physics of Plasmas* 23, 083529 (2016). The total electron number in the jet from µCAP with 20 mm and 60 mm is presented in FIGS. 4A and 4B, and the total electron number for one discharge period is $4.60\times10^{12}$ and $4.04\times10^{12}$, respectively. A very small decrease of electron number has been detected in 60 mm µCAP comparing with 20 mm µCAP.

XTT solution was used to determine the relative concentration of superoxide ($O_2^-$). Superoxide radical reduced soluble formazans of the tetrazolium dye XTT[31,32]. See, Sutherland, M. W. & Learmonth, B. A. The tetrazolium dyes MTS and XTT provide new quantitative assays for superoxide and superoxide dismutase. *Free radical research* 27, 283-289 (1997) and Bartosz, G. Use of spectroscopic probes for detection of reactive oxygen species. *Clinica Chimica Acta* 368, 53-76 (2006).

Figure 4A:
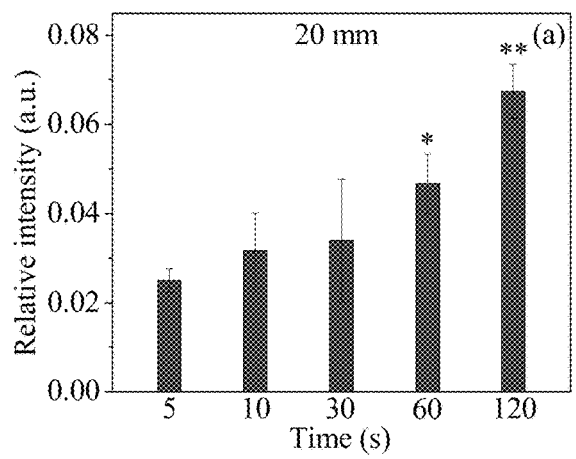
FIGS. 4A-4D show relative $O_2^-$ and •OH concentration of 20 mm and 60 mm μCAP-treated DMEM. For relative $O_2^-$ concentration: (a) 20 mm and (b) 60 mm. For relative •OH concentration: (c) 20 mm and (d) 60 mm. Student t-test was performed, and the statistical significance compared to μCAP 5 s treatment is indicated as *$p<0.05$, $p<0.01$, *$p<0.001$. (n=3).
Figure 4B:
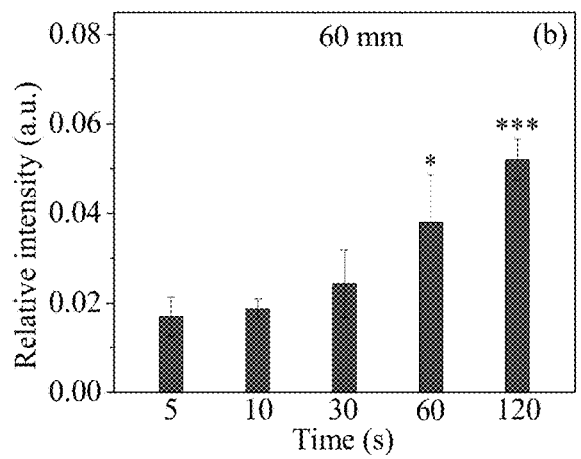
Figure 4C:
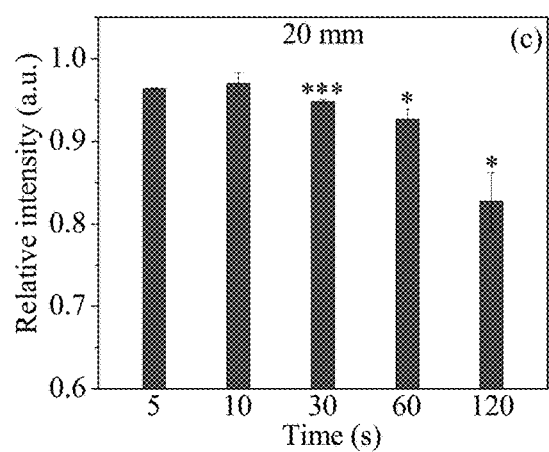
Figure 4D:
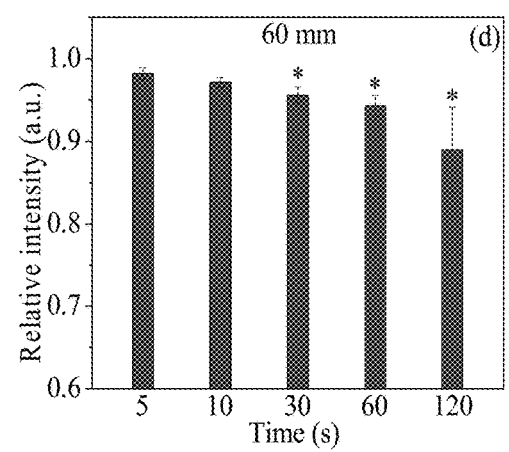

FIGS. 4A and 4D show the relative superoxide concentration of 20 mm and 60 mm µCAP treatment of DMEM. Relative intensity increases with treatment, which corresponds to the relative concentration of superoxide increasing with treatment. Comparing the 20 mm with 60 mm lengths, the 20 mm µCAP device produced a higher relative concentration of superoxide than the 60 mm device. Methylene blue (MB) was used to assess the relative concentration of hydroxyl radicals (•OH). It is known that MB reacts with •OH aqueous solutions, leading to a visible color change[33]. FIGS. 4C and 4D show that the relative MB concentration decreases with the treatment time of µCAP, suggesting that more •OH species are generated in DMEM (20 mm>60 mm). Overall, these findings demonstrate that there is an increase in the relative concentration of $O_2^-$ and •OH as a function of µCAP treatment time.

Figure 5A:
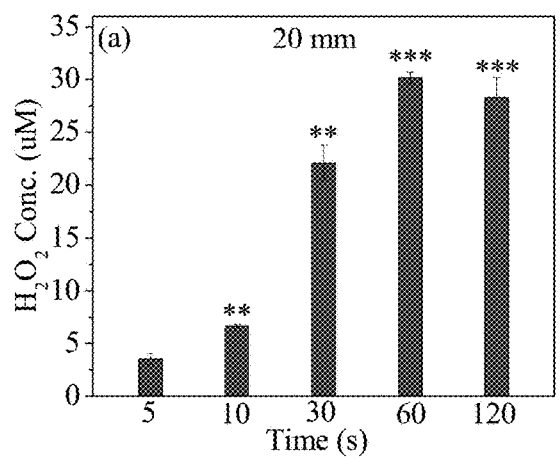
FIGS. 5A-5D show $H_2O_2$ and $NO_2^-$ concentration of 20 mm and 60 mm μCAP-treated DMEM. For $H_2O_2$ concentration: (a) 20 mm and (b) 60 mm. For $NO_2^-$ concentration: (c) 20 mm and (d) 60 mm. Student t-test was performed, and the statistical significance compared to μCAP 5 s treatment is indicated as *$p<0.05$, $p<0.01$, *$p<0.001$. (n=3).
Figure 5B:
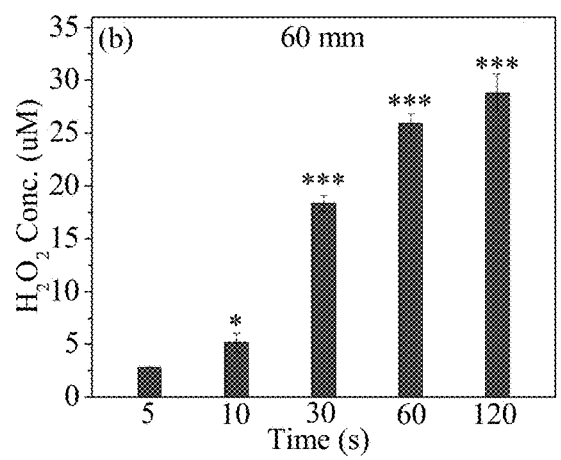
Figure 5C:
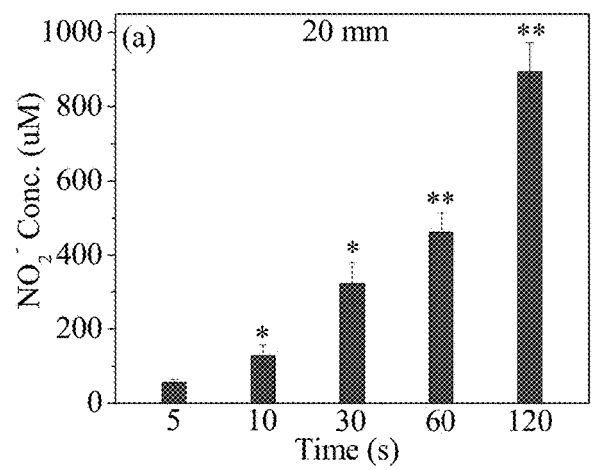
Figure 5D:
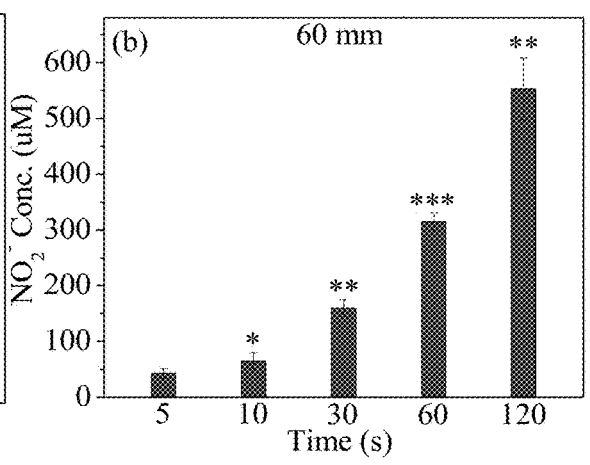
Figure 7A:
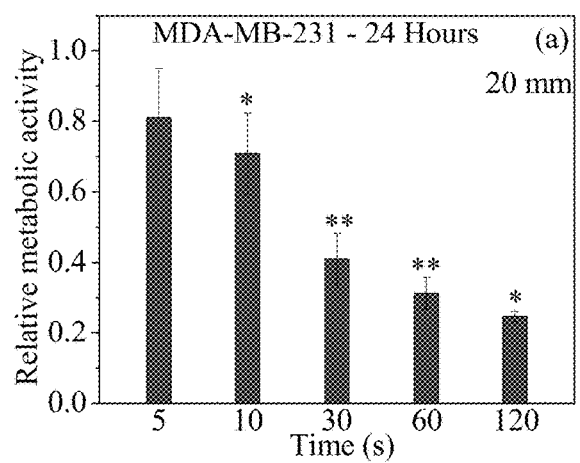
FIGS. 7A-7D show cell viability of MDA-MB-231 after 24 and 48 hours' incubation with μCAP treatment with 20 mm and 60 mm length during 5, 10, 30, 60, and 120 seconds' treatment. Cell viability of MDA-MB-231 treated by 20 mm He μCAP at (a) 24-h incubation and (c) 48-h incubation. Cell viability of MDA-MB-231 treated by 60 mm He μCAP at (b) 24-h incubation and (d) 48-h incubation. The ratios of surviving cells for each cell line were calculated relative to controls (DMEM). Student t-test was performed, and the statistical significance compared to cells present in DMEM is indicated as *$p<0.05$, $p<0.01$, *$p<0.005$. (n=3)
Figure 7B:
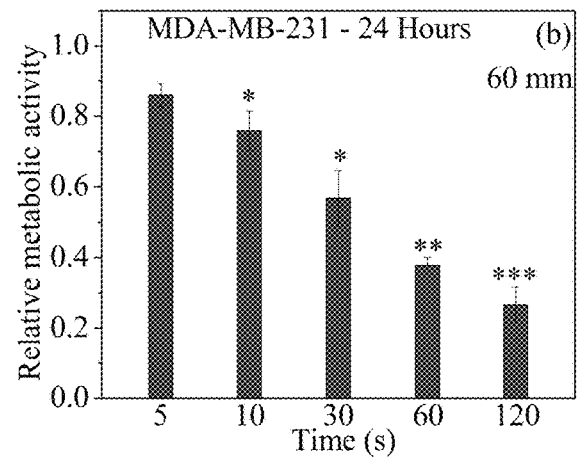
Figure 7C:
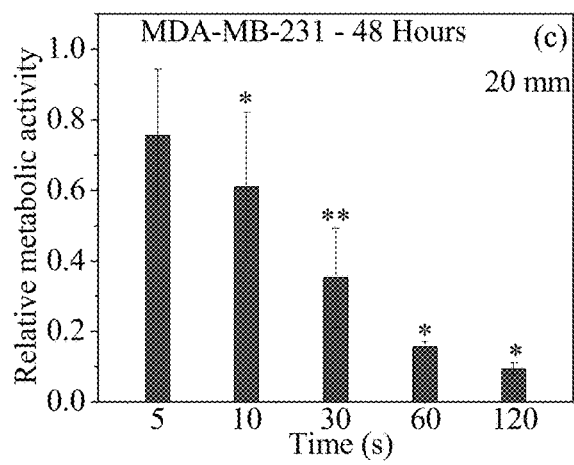
Figure 7D:
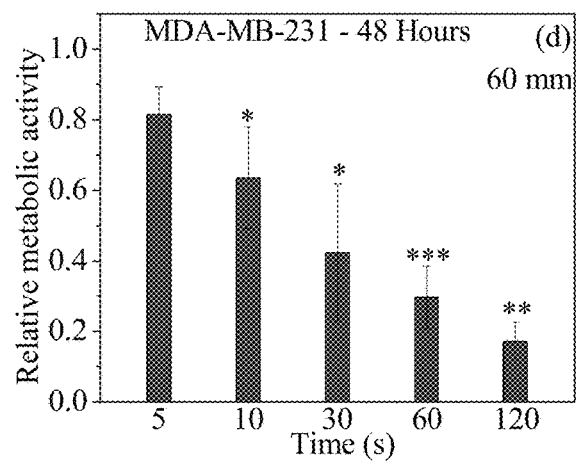

DMEM treated by the 20 mm and 60 mm µCAP induced changes in the concentration of $H_2O_2$ and $NO_2^-$ as a function of the treatment time. These results are shown in FIGS. 5A-5D with concentrations produced by the 20 mm and 60 mm He µCAP devices. In FIG. 5A, the $H_2O_2$ concentrations produced by 20 mm He µCAP device increase with treatment time up to 60 seconds, but between 60 seconds and 120 seconds the concentration decreased. For the $H_2O_2$ concentration produced by 60 mm He µCAP increased with treatment time (In FIG. 5B). It means that the $H_2O_2$ concentration earlier reaches saturation in 20 mm length earlier than with the 60 mm length µCAP device. In FIG. 4, we know that He µCAP produces •OH and $O_2^-$ in DMEM, which are the two most important species in plasma-activated media. In particular, •OH reacting with •OH and $O_2^-$ reacting with $2H^+$ lead to $H_2O_2$ formation[34]. Both $NO_2^-$ concentrations of 20 mm and 60 mm increase with treatment time (in FIG. 5C and FIG. 5D), and $NO_2^-$ concentrations of 20 mm is much higher than 60 mm. Comparing $NO_2^-$ concentration with the $H_2O_2$ concentration under same condition, $NO_2^-$ concentration is much higher than $H_2O_2$ concentration. A possible hypothesis for this result is that DMEM comprises over 30 components such as inorganic salts, amino acids and vitamins, and plasma might react with amino acids to form $NO_2^-$.

FIGS. 6A-6D show the cell viability of the brain (glioblastoma U87) cancer cells after 24 and 48 hours' incubation with µCAP during 5, 10, 30, 60, and 120 seconds' treatment with the 20 mm and 60 mm length µCAP device, respectively. For the 20 mm length µCAP treatment, the cell viability of brain cancer cells was lower than that of the 60 mm length at each treatment duration (from 5 to 60 seconds), and dropped with increasing treatment time. For both 20 mm and 60 mm, 120 seconds' treatment has similar effect on cell viability of U87 cancer cells. For 48 hours' incubation under 20 mm µCAP treatment, 60 and 120 seconds' duration has similar effect on cell viability. Thus, overall conclusion is that 60 mm tube can still produce reactive species while allowing access to deeper tumors.

FIGS. 7A-7D show the cell viability of the breast (MDA-MB-231) cancer cells after 24 and 48 hours' incubation with µCAP treatment with the 20 mm and 60 mm length µCAP devices during 5, 10, 30, 60, and 120 seconds' duration. For both 20 mm and 60 mm µCAP treatment, the cell viability after 24 and 48 hours' incubation dropped with increasing treatment time. For 20 mm µCAP treatment, the cell viability of breast cancer cells was lower than that of the 60 mm length at each treatment duration.

Figure 2B:
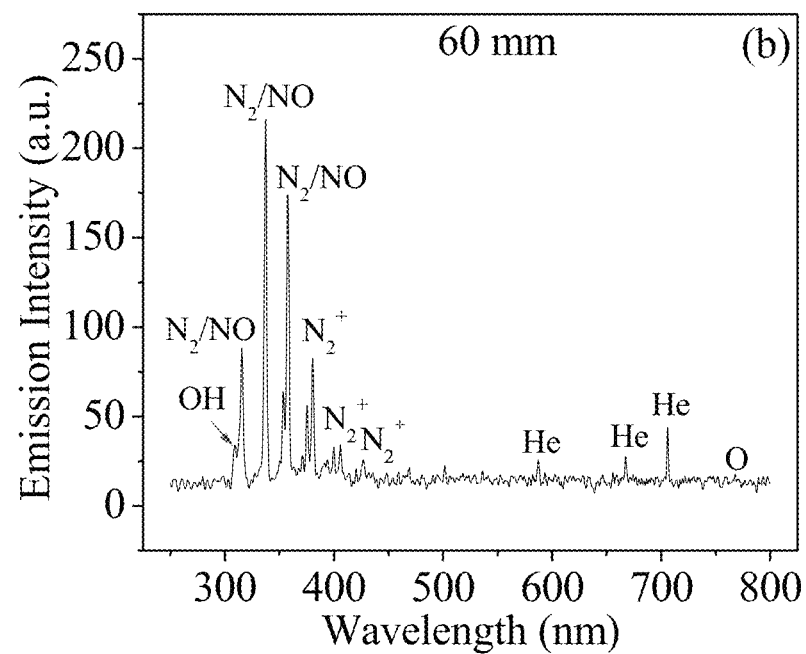

The direct plasma jet irradiation is limited to the skin and it can also be invoked as a supplement therapy during surgery as it only causes cell death in the upper three to five cell layers. However, the current cannulas from which the plasma emanates are too large for intracranial applications. Thus, we developed a micro-sized plasma devices with 20 mm and 60 mm length stainless steel tubes, which both can achieve effective killing of brain and breast cancer cells. This preliminary study offers significant potential for new treatment applications. Numerous studies reported plasma-induced apoptosis in cancer cells due to plasma-generated various reactive species[1,35,36]. Plasma generates various kinds of ROS and RNS, including hydrogen peroxide ($H_2O_2$), ozone ($O_3$), hydroxyl radical (•OH), atomic oxygen (O), superoxide ($O_2^-$), nitric oxide (NO) and peroxynitrite anion ($ONOO^-$), singlet delta oxygen ($O2(^1\Delta g)$), nitrite ($NO_2^-$) and are displayed in FIG. 2. See, Graves, D. B. The emerging role of reactive oxygen and nitrogen species in redox biology and some implications for plasma applications to medicine and biology. *Journal of Physics D: Applied Physics* 45, 263001 (2012) and Laroussi, M. & Leipold, F. Evaluation of the roles of reactive species, heat, and UV radiation in the inactivation of bacterial cells by air plasmas at atmospheric pressure. *International Journal of Mass Spectrometry* 233, 81-86 (2004). In this description, we have specifically measured relative concentrations of $O_2^-$ and •OH (short-lived species, FIG. 4) and the concentration of $H_2O_2$ and $NO_2^-$ (long-lived species, FIG. 5). The relative concentration of $O_2^-$ treated by µCAP with 20 mm and 60 mm increases with treatment time (FIGS. 4A and 4B). $O_2^-$ can activate mitochondrial-mediated apoptosis by changing mitochondrial membrane potential and simultaneously up-regulates pro-apoptotic genes and down-regulates anti-apoptotic genes for activation of caspases resulting in cell death. See, Riedl, S. J. & Shi, Y. Molecular mechanisms of caspase regulation during apoptosis. *Nature reviews Molecular cell biology* 5, 897-907 (2004). FIGS. 4C and 4D shows the relative concentration of •OH in DMEM treated by µCAP with 20 mm and 60 mm also increases with treatment time. •OH derived amino acid peroxides can contribute to cell injury because •OH itself and protein (amino acid) peroxides are able to react with DNA, thereby inducing various forms of damage. See, Adachi, T. et al. Plasma-activated medium induces A549 cell injury via a spiral apoptotic cascade involving the mitochondrial-nuclear network. *Free Radical Biology and Medicine* 79, 28-44 (2015). Compared with cell viability of both cancer lines, the trend of cell death can be partly attributed to the increase of $O_2^-$ and •OH concentration with treatment time. On the other hand, the 20 mm µCAP device shows higher relative concentrations of $O_2^-$ and •OH, such that the 20 mm µCAP device is more effective in killing both cancer cell lines than the 60 mm µCAP device. FIG. 5 shows $H_2O_2$ and $NO_2^-$ concentration of the 20 mm and 60 mm µCAP-treated DMEM. $H_2O_2$ can induce cell death by apoptosis and necrosis, while $NO_2^-$ are known to induce cell death via DNA damage. See, Chen, Z. et al. A novel micro cold atmospheric plasma device for glioblastoma both in vitro and in vivo. *Cancers* 9, 61 (2017) and Boehm, D., Heslin, C., Cullen, P. J. & Bourke, P. Cytotoxic and mutagenic potential of solutions exposed to cold atmospheric plasma. *Scientific reports* 6, 21464 (2016). Thus, the synergism of $H_2O_2$ and $NO_2^-$ might be an important factor in cancer cells killing efficiency.

Several methods are now being used for the cancer treatment such as chemotherapy, surgery, and radiotherapy. See, for example, Arap, W., Pasqualini, R. & Ruoslahti, E. Cancer treatment by targeted drug delivery to tumor vasculature in a mouse model. *Science* 279, 377-380 (1998); Morris, T., Steven Greer, H. & White, P. Psychological and social adjustment to mastectomy. A two-year follow-up study. *Cancer* 40, 2381-2387 (1977); and Delaney, G., Jacob, S., Featherstone, C. & Barton, M. The role of radiotherapy in cancer treatment. *Cancer* 104, 1129-1137 (2005). The conventional methods have some disadvantages such as low rapidity, high cost, and adverse effects. However, plasma treatment may overcome these disadvantages of the traditional treatments. Currently, plasma can be directly applied to skin cancers, while it is not applicable for more systemic cancer treatment. However, we developed novel µCAP with 20 mm and 60 mm length can be considered as a local treatment tool and does not exert the systemic therapeutic effects like chemical drugs, meanwhile removing limits of plasma itself. Overall, the above results and discussion indicate that both µCAP with 20 mm and 60 mm length might be useful and should be considered in a clinical medical application.

In presently application, we disclose newly developed micro-sized cold atmospheric plasma (µCAP) with 20 mm and 60 mm length stainless steel tubes inducing the production of reactive species and radicals in culture medium. There is an increase in the concentration of $O_2^-$, •OH, $H_2O_2$, and $NO_2^-$ as a function of µCAP treatment time, which matches the trend of cell viability of two cancer cells with µCAP treatment time. A synergistic effect of short- and long-lived species present in the plasma treating DMEM is suspected to play a key role in cell death. Even µCAP with 60 mm length still have serious effect on both U87 and MDA-MB-231 cancer cells, and can produce reactive species allowing access to deeper tumors. The results of this study suggest a possibility for clinical applications of µCAP on brain and breast tumor.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A micro-sized cold atmospheric plasma surgical accessory comprising:
   a tube;
   an active electrode within said tube; and
   a nozzle at a distal end of said tube, said nozzle having an inner diameter less than 1 mm and a length greater than 15 mm and less than 30 mm;
   wherein a distal end diameter of said tube is greater than said inner diameter of said nozzle.

2. A micro-sized cold atmospheric plasma surgical accessory according to claim 1, wherein said nozzle is 15-25 mm in length.

3. A micro-sized cold atmospheric plasma surgical accessory according to claim 1, wherein said nozzle comprises stainless steel.

4. A micro-sized cold atmospheric plasma surgical accessory according to claim 1, wherein said tube has an inner diameter greater than 1 mm.

5. A micro-sized cold atmospheric plasma surgical accessory according to claim 1, wherein said nozzle has a distal end inner diameter less than 280 µm.

6. A micro-sized cold atmospheric plasma surgical accessory according to claim 1, further comprising a return electrode on an outside of said tube.

7. A micro-sized cold atmospheric plasma surgical accessory according to claim 3, wherein said tube comprises a quartz tube.

8. A method for treating cancerous tissue with cold atmospheric plasma comprising:
   causing an inert gas to flow through a tube toward target tissue;
   applying electrosurgical energy to an electrode within said tube to plasmatize gas flowing through said tube;
   causing said plasma to flow out of a nozzle at a distal end of said tube, said nozzle having an inner diameter less than 1 mm and a length greater than 15 mm and less than 30 mm; and
   applying said plasma flowing out of said nozzle to target tissue.

9. A method for performing cold atmospheric plasma treatment according to claim 8, wherein said nozzle has a constant inner diameter of less than 280 µm.

10. A micro-sized cold atmospheric plasma surgical accessory comprising:
    a first tube;
    an active electrode within said first tube; and
    a second tube at a distal end of said first tube, said second tube having a constant inner diameter less than 1 mm and a length greater than 15 mm and less than 30 mm;
    wherein a distal end diameter of said first tube is greater than said inner diameter of said second tube.

* * * * *